United States Patent [19]

Della Valle et al.

[11] Patent Number: 5,925,678

[45] Date of Patent: *Jul. 20, 1999

[54] USE OF N-ACYL DERIVATIVES OF AMINOALCOHOLS IN THE MANUFACTURE OF A MEDICAMENT FOR PRACTICING NEUROPROTECTIVE ACTION IN NEUROPATHOLOGICAL STATES CONNECTED WITH EXCITOTOXICITY

[75] Inventors: Francesco Della Valle; Alberta Leon; Silvana Lorenzi, all of Padova, Italy

[73] Assignee: Lifegroup S.P.A., Monselice, Italy

[ * ] Notice: This patent is subject to a terminal disclaimer.

[21] Appl. No.: 08/714,113

[22] PCT Filed: Mar. 17, 1995

[86] PCT No.: PCT/EP95/01002

§ 371 Date: Sep. 23, 1996

§ 102(e) Date: Sep. 23, 1996

[87] PCT Pub. No.: WO95/25509

PCT Pub. Date: Sep. 28, 1995

[30] Foreign Application Priority Data

Mar. 21, 1994 [IT] Italy ............................... MI94A0523

[51] Int. Cl.$^6$ ................................................ A61K 31/155
[52] U.S. Cl. ............................................ 514/566; 514/625
[58] Field of Search ...................... 514/566, 625

[56] References Cited

U.S. PATENT DOCUMENTS 5,227,397  7/1993  Saccomano et al. .
5,618,842  4/1997  Della Valle et al. .................. 514/566

FOREIGN PATENT DOCUMENTS

A -177245   4/1986   European Pat. Off. .
A -550008   7/1993   European Pat. Off. .
A -570714  11/1993   European Pat. Off. .
A -932503  12/1993   WIPO .

OTHER PUBLICATIONS

John W. Olney "Excitotoxic Amino Acids and Neuropsychiatric Disorder" 1990, pp. 47–71.

R. Dubner et al. "Activity–Dependent Neuronal Plasticity Following Tissue Injury and Flammation." 1992 pp. 96–103.

Uwe Otten eual. "Nerve Growth Factor Induces Growth and Differentiation of Human B Lynphocytes ." Dec. 1989, pp. 10059–10063

Jean S. Marshall et al. "The Role of Mast Cell Degranulation Products in Mast Cell Hyperplasia" Mar. 1, 1990., pp. 1886–1892.

Anthony N. Van Den Pol et al. "Glutarnate Neurons in Hypothalamus Regulate Excitatory Transmission" Jul. 1993, 2829–2838.

Melvyn P. Heyes, PhD, et al ., Quinolinic Acid in Cerebrospinal Fluid and Serum HIV–1 Infection Relationship to Clinical and Neurolgical Status Aug. 26, 1990, pp. 202–209.

Primary Examiner—Keith D. MacMillan
Attorney, Agent, or Firm—McDermott, Will & Emery

[57] ABSTRACT

The use of N-acyl derivatives of aminoalcohols with mono- and di-carboxylic acids for the prevention and treatment of diseases connected with hyper and prolonged excitation by excitatory amino acids is described.

8 Claims, No Drawings

USE OF N-ACYL DERIVATIVES OF AMINOALCOHOLS IN THE MANUFACTURE OF A MEDICAMENT FOR PRACTICING NEUROPROTECTIVE ACTION IN NEUROPATHOLOGICAL STATES CONNECTED WITH EXCITOTOXICITY

FIELD OF THE INVENTION

The present invention relates to the use of N-acyl derivatives of aminoalcohols with mono and dicarboxylic acids for the prevention and treatment of neuropathological states connected with excitotoxicity.

PRIOR ART DISCLOSURE

Recent research has established that the nervous system is not an isolated entity but a component of a complex inter-communication system together with the main homeostatic systems—immune system and endocrine system—where stimuli from one of the three systems are received and adaptive responses are processed by the other two in order to maintain or regulate homeostatic equilibrium in the body. In fact, although the nervous system, the endocrine system and the immune system utilize languages of their own, they can translate and process the messages received from the other systems.

Scientific literature has recently reported some results suggesting that the mast cell, an immunocompetent cell ubiquitously present in tissues, might be the element providing communication between the three systems: due to the anatomic dislocation—in proximity of nerve endings and in contiguity with the vascular system—and to its functional role being evidenced, said cell might be capable of acting as a "gate keeper" within said complex system.

Following tissue injury, stimuli capable of activating mast cells are produced leading to the prompt release from preformed stores of mediators and other substances with chemotactic, proinflammatory and cytotoxic effects. Cytokines (TNF-α and interleukins), vasoactive amines (serotonin, bradikinin and histamine), heparin and PAF are some examples.

The presence of mediators and kinins at the site of injury increases the sensitivity to pain in the acute stage; further, the accumulation of IL-1, IL-3 and TNF-α induces the synthesis of NGF which locally increases the proinflammatory agonist stimulus (mast cell and T-lymphocyte proliferation, mast cell degranulation), which is thus amplified and prolonged (U. Otten et al., 1989, "Nerve Growth Factor induces growth and differentiation of human lymphocytes", *PNAS* 86: 10059–10063; J. S. Marshall et al., 1989, "The role of mast cell degranulation product in mast cell hyperplasia", *The J. of Immunology,* 144: 1886–1892) having the consequence of inducing modifications in the number of nerve endings and facilitate these inflammatory conditions to become chronic (R. Dubner and M. A. Ruda, 1992, "Activity-dependent neuronal plasticity following tissue injury and inflammation", *TINS,* 15, 3: 96–103).

These and further evidences for the susceptibility and rapidity of mast cell degranulation phenomena suggested the need for an inhibitory control. In addition to the corticosteroid-mediated pleiotropic control, already characterized, a local control system has been developed by the Applicant, said system being pharmacologically applicable with specific compounds structurally related to endogenous autacoids and chemically definable as N-acyl lipids, as disclosed in European patent applications No. 92121862.4 published with No. 0 550 006 A3 and No. 92121864.0 published with No. 0 550 008 A2.

The experimental evidence obtained by the Applicant for these N-acyl lipids proved the presence of a local antagonist endogenous regulation mechanism, meant to control mast cell degranulation induced by neurogenic and immunogenic supramaximal stimuli (ALIA=Autacoid Local Inflammation Antagonism). Said discovery is of great pharmacological importance, making it possible to synthesize drugs, chemically definable as N-acyl derivatives of mono and polycarboxylic acid with aminoalcohols, which can act as autacoids with the ability to modulate mast cell activation associated to neuroimmunogenic inflammatory processes in autoimmune diseases and other pathological conditions (see the aforementioned patent applications).

SUMMARY OF THE INVENTION

The Applicant has surprisingly found that compounds belonging to the class of N-acyl derivatives of mono and dicarboxylic acids with aminoalcohols which can exert a protective action against the neurotoxicity induced by excitatory amino acids (EAA), such as glutamic acid (hereinafter referred to as Glu), in neuronal cultures, when incubated at the same time or after exposure to the excitotoxic stimulus. The kinetics of this effect makes said compounds of high applicative interest in acute and chronic disorders of the central nervous system. Therefore, the present invention is related to the use of said N-acyl derivatives and of more soluble and/or slow release derivatives thereof as active principles in the preparation of pharmaceutical compositions for the prevention and treatment of acute and chronic diseases of the central nervous system connected with EAA neurotoxicity.

The compounds according to the present invention are defined by the following formulas (I) and (II):

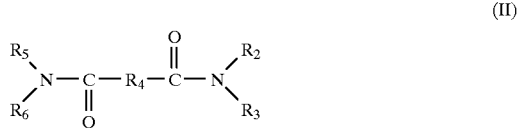

where

is the acyl radical of a linear or branched, saturated or unsaturated aliphatic monocarboxylic acid, containing 2 to 20 carbon atoms, optionally substituted in the aliphatic chain with one of more hydroxyl, aminic, ketonic, carboxyl, cycloalkyl, aryl, heterocyclic, aromatic, heteroaromatic, polycyclic groups; or the acyl radical of an aromatic, heteroaromatic or heterocyclic monocarboxylic acid;

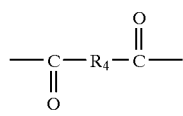

is the diacyl radical of a saturated or unsaturated aliphatic dicarboxylic acid, optionally substituted with an aminic, hydroxyl or ketonic group; or the diacyl radical of an aromatic, heterocyclic or heteroaromatic dicarboxylic acid;

$R_2$ and $R_5$ are alcoholic residues selected from a $C_1$–$C_{20}$ linear or branched hydroxyalkyl, optionally substituted in the aliphatic chain with one or more aryl groups, and a hydroxyaryl optionally substituted with one or more linear or branched alkyl radicals of from 1 to 20 carbon atoms; in both cases, the hydroxyl group is optionally esterified to —OX, wherein X is the acyl radical of a linear or branched, saturated or unsaturated, aliphatic acid, optionally substituted in the aliphatic chain with one or more aryl groups or with one —COOH optionally salified, or X is the acyl radical of an aromatic acid or —$PO_3H_2$ optionally salified;

$R_3$ is H or $R_2$;

$R_6$ is H or $R_5$.

DETAILED DESCRIPTION OF THE INVENTION

The characterization and advantages of N-acyl derivatives of mono and dicarboxylic acids of aminoalcohols as active compounds able to counteract the neuronal death induced by excitotoxic event and, therefore, useful for the treatment of diseases connected with a hyper and prolonged stimulation of EAA receptors will be described in detail hereinafter.

In the derivatives of formula (I), when

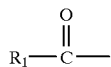

the acyl radical of a saturated or unsaturated aliphatic monocarboxylic acid, it is preferably selected from the group consisting of acetic, caproic, butyric, palmitic, oleic, stearic, lauric, linoleic, linolenic and myristic acid and hydroxyl, aminic and ketonic homologues thereof, glycolic, pyruvic, lactic, caprylic, valeric, valproic, arachidonic acid, gamma-trimethyl-β-hydroxybutyrobetaine and derivatives thereof acylated on the hydroxyl group;

when

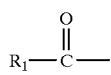

is the acyl radical of an aromatic, heteroaromatic or heterocyclic monocarboxylic acid, it is preferably selected from the group consisting of salicylic, acetylsalicylic, benzoic, trimethoxybenzoic, isonicotinic, thenoic, phenylanthranilic, retinoic, hydroxyphenylaceric, α-lipoic (thioctic) and deoxycholic acid.

In the derivatives of formula (II), when

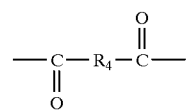

is the diacyl radical of a saturated or unsaturated aliphatic dicarboxylic acid, it is preferably selected from the group consisting of oxalic, fumaric, azelaic, succinic, traumatic, glutaric and muconic acid and hydroxyl, aminic and ketonic homologs thereof, malic, aspartic and tartaric acid;

when

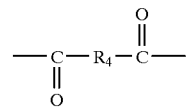

is the diacyl radical of an aromatic, heteroaromatic or heterocyclic dicarboxylic acid, it is preferably selected from the group consisting of phthalic, folic and chromoglycic acid.

$R_2$, $R_3$, $R_5$, and $R_6$, are preferably radicals of aminoalcohols selected from the group consisting of monoethanolamine, diethanolamine, 2-hydroxypropylamine and di-(2-hydroxypropyl)-amine, wherein the hydroxyl group is optionally esterified to aliphatic esters, araliphatic esters, aromatic esters, O-phosphates, acid hemiesters or salified derivatives thereof.

Therefore, with reference to formula (I), the compounds of the present invention have preferably the following structures:

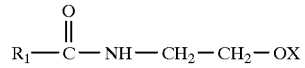

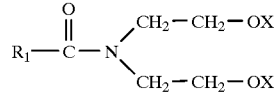

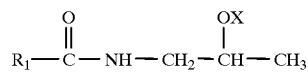

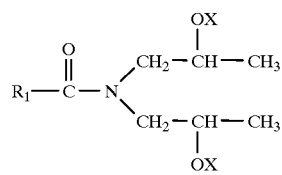

where X is H, —$PO_3H_2$, optionally salified with monovalent or bivalent inorganic ions, or X is the acyl radical of a linear or branched, saturated or unsaturated, aliphatic carboxylic acid, optionally substituted on the aliphatic chain with one or more aryl groups or with one —COOH optionally salified with monovalent or bivalent inorganic ions, and is preferably

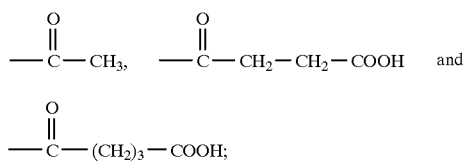

or X is the acyl radical of an aromatic carboxylic acid, preferably benzoic acid.

Said monovalent or bivalent inorganic ions are preferably K, Na, Mg or Ca.

With reference to formula (II), the compounds of the present invention have preferably the following structures:

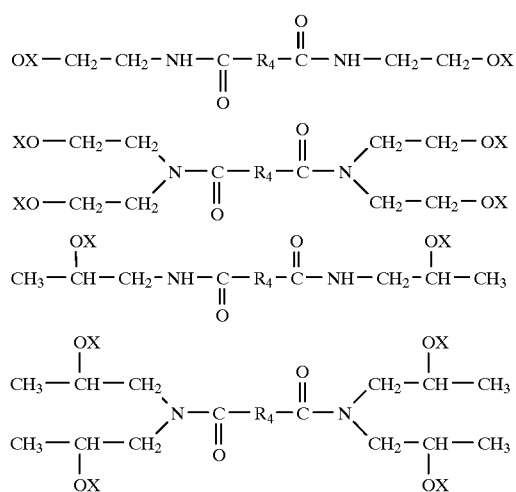

where X is defined as above.

It is to be noted that chemical group X serves to increase the solubility in water and/or to modify the pharmacokinetic properties of the compound, giving a pro-drug.

It is also to be noted that the derivatives of the aminoalcohols 2-hydroxypropylamine and di-(2-hydroxypropyl)-amine can be racemic or optical isomers.

The compounds according to the present invention are prepared by the different methods described hereinbelow.

Method of Synthesis A

High-temperature melting of alkanolamine salt with a carboxylic acid, with formation of the relevant alkanolamide.

Procedure

A mixture consisting of a carboxylic acid and an alkanolamine (1:1.5 equivalents) is fed to a flask provided with reflux condenser and heated to 130–160° C., for 4 to 8 hrs, on an oil bath. The alkanolamide obtained is purified by a method or by a combination of methods reported below:

fractional distillation in vacuo;

liquid/liquid extraction;

crystallization from a suitable solvent or mixture of volatile solvents, selected from the classes of alcohols, ketones, esters, ethers, hydrocarbons or chlorinated solvents;

liquid chromatography using an ion exchange resin, silica gel or alumina as stationary phase, or a reversed phase adsorbent selected among those available on the market, consisting of polymers or silica.

Method of Synthesis B

N-acylation of an alkanolamine with a suitable carboxylic acid activated derivative.

Procedure

An alkanolamine solution in a suitable solvent or mixture of solvents, selected from the group consisting of water, alcohols, ketones, esters, ethers, chlorinated solvents, dialkylamides, dialkylsulphoxides and heterocycles, is cold stirred. The carboxylic acid activated derivative (acyl halide, anhydride or alkylester) is added slowly over a period of 30 min to 3 hrs.

Acylation can be carried out in the presence of a suitable base, selected from the group consiting of hydroxides, inorganic carbonates and bicarbonates and organic tertiary amines, at a temperature ranging from –20° C. to +120° C. The alkanolamide obtained is purified by a method or by a combination of methods as per Method A.

Method of Synthesis C

Activation of the carboxylic acid with alkylchloroformate, followed by aminolysis of the obtained mixed anhydride with alkanolamine.

Procedure

A carboxylic acid solution in a suitable organic solvent, selected from the group consisting of ketones, esters, ethers, chlorinated solvents, dialkylamides, dialkylsulphoxides and heterocycles, is cold stirred at a temperature ranging from –20° C. to +30° C. An equivalent quantity of alkylchloroformate is added slowly, over a period of 30 min to 3 hrs.

Activation is carried out in the presence of a suitable weak base, selected from the group consisting of inorganic carbonates and bicarbonates and organic tertiary amines, at a temperature ranging from –20° C. to +30° C.

The obtained mixed anhydride is subjected to aminolysis by addition of an equivalent quantity of alkanolamine, still at low temperature.

The alkanolamide obtained is purified by a method or by a combination of methods as per Method A.

Some preparation examples of the compounds of formulas (I) and (II) according to the present invention and their biological activities are reported hereinbelow for illustrative but not limitative purposes.

EXAMPLE 1

Preparation of N-(2-Hydroxyethyl)-Palmitoylamide

Following the method described by Roe et al. (J.Am.Chem.Soc., 74, 3442–3443, 1952), palmitic acid (2.56 g; 1 mmol) was caused to react with ethanolamine (0.9 g; 1.5 mmol) by refluxing in ethyl ether, under nitrogen atmosphere, for 5 to 6 hrs.

The product obtained was extracted from the reaction mixture and crystallized from 95% ethyl alcohol at 0° C.

The physico-chemical properties of N-(2-hydroxyethyl)-palmitoylamide were as follows:

| | |
|---|---|
| physical state | crystalline powder |
| molecular formula | $C_{18}H_{37}NO_2$ |
| molecular weight | 299.48 |
| elemental analysis | C = 72.19%; H = 12.45%; N = 4.68%; O = 10.69% |
| solubility in organic solvents | hot methanol, $CH_3Cl$, DMSO |
| solubility in water | insoluble |
| melting point | 94–95° C. |
| TLC | eluent: chloroform-methanol, 9/1 Rf = 0.75 |

EXAMPLE 2

Preparation of N-(2-Acetoxyethyl)-Palmitoylamide

N-(2-hydroxyethyl)-palmitoylamide (see Example 1) (3.0 g; 10 mmol) was solubilized in anhydrous pyridine (30 ml)

under stirring at 0° C. and added with acetic anhydride (1.53 g; 15 mmol). The resulting solution was stirred at 0° C. for a period of 15 min and heated to 45° C. for 24 hrs. The reaction mixture was evaporated to dryness in vacuo. The residue was taken up with methanol (30 ml) and evaporated to dryness in vacuo. The residue was crystallized from methanol (50 ml) and the crystalline fraction was separated by filtration, washed three times with cold methanol (10×3 ml) and finally dried in high vacuo.

The reaction yield was 93% approx.

The physico-chemical properties of N-(2-acetoxyethyl)-palmitoylamide were as follows:

| | |
|---|---|
| physical state | white crystalline powder |
| molecular formula | $C_{20}H_{39}NO_3$ |
| molecular weight | 341.54 |
| elemental analysis | C = 70.34%; H = 11.51%; N = 4.10%; O = 14.05% |
| solubility in organic solvents | >5 mg/ml in n-octanol |
| solubility in water | poorly soluble |
| melting point | 78–81° C. |
| TLC | eluent: chloroform-methanol, 95/5 Rf = 0.58 |

EXAMPLE 3

Preparation of N-(2-Acetoxyethyl)-Benzoylamide

N-(2-hydroxyethyl)-benzoylamide (1.65 g; 10 mmol), prepared according to Example 8 of the European patent application published with No. 0 550 006, was solubilized in anhydrous pyridine (15 ml) under stirring at 0° C. and added with acetic anhydride (1.53 g). The resulting solution was stirred at 0° C. for a period of 15 min and heated to 45° C. for 24 hrs. The reaction mixture was evaporated to dryness in vacuo. The residue was taken up with water (30 ml) and extracted twice with ethyl acetate (20×2 ml). The organic phases were washed twice with 1 N HCl (10×2 ml), once with water (10 ml), twice with 5% $NaCOH_3$ (10×2 ml) and once with water (10 ml). They were then combined, dehydrated with $Na_2SO_4$, evaporated to dryness in vacuo. The residue was crystallized from tert-butylmethyl ether (20 ml) and the crystalline fraction was separated by filtration, washed twice with cold tert-butylmethyl ether (5×2 ml) and finally dried in high vacuo.

The reaction yield was 85% approx.

The physico-chemical properties of N-(2-acetoxyethyl)-benzoylamide were as follows:

| | |
|---|---|
| physical state | white crystalline powder |
| molecular formula | $C_{11}H_{13}NO_3$ |
| molecular weight | 207.23 |
| elemental analysis | C = 63.76%; H = 6.32%; N = 6.76%; O = 23.16% |
| solubility in organic solvents | >10 mg/ml in n-octanol; >10 mg/ml in DMSO |
| solubility in water | poorly soluble |
| melting point | 52.5–54.5° C. |
| TLC | eluent: chloroform-methanol-water-$NH_3$ (30%), 80/25/2/1 Rf = 0.77 |

EXAMPLE 4

Preparation of N,N'-Bis(2-Acetoxyethyl)-Fumaroylamide

N,N'-bis(2-hydroxyethyl)-fumaroyldiamide (2.02 g; 10 mmol), prepared according to Example 1 of the European patent application published with No. 0 550 008, was solubilized in anhydrous pyridine (20 ml) under stirring at 0° C. and added with acetic anhydride (3.06 g; 30 mmol). The resulting solution was stirred at 0° C. for a period of 15 min and heated to 45° C. for 24 hrs. The reaction mixture was evaporated to dryness in vacuo. The residue was taken up with methanol (30 ml) and evaporated to dryness in vacuo. The residue was crystallized from absolute ethanol (50 ml) and the crystalline fraction was separated by filtration, washed three times with cold ethanol (5×3 ml) and finally dried in high vacuo.

The reaction yield was 91% approx.

The physico-chemical properties of N,N'-bis(2-acetoxyethyl)-fumaroylamide were as follows:

| | |
|---|---|
| physical state | white crystalline powder |
| molecular formula | $C_{12}H_{18}N_2O_6$ |
| molecular weight | 286.29 |
| elemental analysis | C = 50.35%; H = 6.33%; N = 9.79%; O = 33.53% |
| solubility in organic solvents | >10 mg/ml in DMSO |
| solubility in water | poorly soluble |
| melting point | 214–216° C. |
| TLC | eluent: chloroform-methanol-water-$NH_3$ (30%), 80/25/2/1 Rf = 0.81 |

EXAMPLE 5

Preparation of N-Palmitoylethanolamide Phosphate

N-(2-hydroxyethyl)-palmitoylamide (see Example 1) (3.0 g; 10 mmol) was solubilized in anhydrous methanesulphonic acid (10 ml) under stirring at 0° C. and added with phosphoric anhydride (2.12 g; 15 mmol). The resulting mixture was stirred at 0° C. for a period of 25 hrs. The reaction mixture was added with ether until product precipitation was complete. The precipitate was separated by centrifugation, dried in vacuo, washed with cold water and finally dried in vacuo. The crude product obtained was hot washed with tert-butylmethyl ether (50 ml) and crystallized from isopropanol (50 ml). The crystalline fraction was separated by filtration, washed three times with cold isopropanol (10×3 ml) and finally dried in high vacuo.

The reaction yield was 83% approx.

The physico-chemical properties of N-palmitoylethanolamide phosphate were as follows:

| | |
|---|---|
| physical state | white crystalline powder |
| molecular formula | $C_{18}H_{38}NO_5P$ |
| molecular weight | 379.48 |
| elemental analysis | C = 56.97%; H = 10.09%; N = 3.69%; O = 21.08%; P = 8.16% |
| solubility in organic solvents | >10 mg/ml in DMSO |
| solubility in water | poorly soluble (>1 mg/ml in 50 mM phosphate buffer, pH 7.4, NaCl 0.9%) |
| melting point | undeterminable |
| TLC | eluent: chloroform-methanol-water-$NH_3$ (30%), 50/40/7/3 Rf = 0.38 |

EXAMPLE 6

Preparation of N,N'-Bis(2-Hydroxyethyl)-Dodecenediamide Diphosphate Disodium Salt Traumatic acid (2.28 g; 10 mmol) and N-hydroxysuccinimide (2.42 g; 21 mmol) were solubilized in anhydrous pyridine (50 ml) under stirring at 0° C. and added with dicyclohexylcarbodiimide (4.33 g; 21 mmol). The resulting mixture was stirred at 0° C. for a period of 1 hr and further stirred at room temperature for a period of 20 hrs. The resulting suspension was filtered, the precipitate removed and the solution evaporated to dryness in vacuo. The crude residue was solubilized in DMF (50 ml), added with triethylamine (5.05 g; 50 mmol) and stirred at 0° C. O-phosphocholamine (2.96 g; 21 mmol) was solubilized in cold water (10 ml) and the resulting solution was added dropwise to the succinimide ester solution over a period of 1 hr. The mixture was further stirred at room temperature for a period of 24 hrs and finally evaporated to dryness in high vacuo. The residue was taken up with water (20 ml) and eluted in a column containing 70 ml of cationic exchange resin Dowex 50×8, generated in the H+ form. The eluate was neutralized to pH 7.0 with 5% $Na_2CO_3$ solution and concentrated in vacuo to 5 ml by vol. approx. The oily residue was purified by reverse phase chromatography in Lichrosorb RP18 R column, eluting with water. The fractions containing the pure product were combined and lyophilized.

The reaction yield was 78% approx.

The physico-chemical properties of N,N'-bis-(2-hydroxyethyl)-dodecenediamide diphosphate disodium salt were as follows:

| | |
|---|---|
| physical state | white amorphous powder |
| molecular formula | $C_{16}H_{30}N_2O_{10}P_2Na_2$ |
| molecular weight | 518.35 |
| elemental analysis | C = 37.07%; H = 5.83%; N = 5.40%; O = 30.87%; P = 11.95%; Na = 8.87% |
| solubility in organic solvents | >10 mg/ml in DMSO (product in acid form) |
| solubility in water | >10 mg/ml |
| melting point | 214–216° C. |
| TLC | eluent: ethanol/water/acetic acid, 70/20/10 Rf = 0.47 |

EXAMPLE 7

Preparation of N-(2-Hydroxyethyl)-Palmitoylamide Succinate Acid

N-(2-hydroxyethyl)-palmitoylamide (3.0 g; 10 mmol) (see Example 1) was added with succinic anhydride (1.5 g; 15 mmol) and anhydrous sodium acetate (50 mg). The mixture was heated to 120° C. with continued stirring, under nitrogen atmosphere, and cooled to room temperature. The crude product obtained was crystallized from a 0:30 ethanol-water mixture (50 ml). The precipitate was separated by filtration, washed three times with cold ethanol (10×3 ml) and finally dried in high vacuo.

The reaction yield was 94% approx.

The physico-chemical properties of N-(2-hydroxyethyl)-palmitoylamide succinate acid were as follows:

| | |
|---|---|
| physical state | white crystalline powder |
| molecular formula | $C_{22}H_{41}NO_5$ |
| molecular weight | 399.58 |
| elemental analysis | C = 66.13%; H = 10.34%; N = 3.51%; O = 20.02% |
| solubility in organic solvents | >5 mg/ml in DMSO |
| solubility in water | poorly soluble (>1 mg/ml as potassium salt) |
| melting point | 115–118° C. |
| TLC | eluent: chloroform-methanol-water-$NH_3$ (30%), 80/25/2/1 Rf = 0.22 |

EXAMPLE 8

Preparation of N,N'-Bis(2-Hydroxyethyl)-Dodecenediamide Disuccinate Acid

N,N'-bis(2-hydroxyethyl)-dodecenediamide (3.14 g; 10 mmol) prepared according to Example 6 of the European patent application published with No. 0 550 008, was added with succinic anhydride (3.0 g; 30 mmol) and anhydrous sodium acetate (100 mg). The mixture was heated to 120° C. for 3 hrs with continued stirring, under nitrogen atmosphere, and cooled to room temperature. The crude product obtained was crystallized from a 70:30 ethanol-water mixture (50 ml). The precipitate was separated by filtration, washed three times with cold ethanol (10×3 ml), and dried in high vacuo.

The reaction yield was 89% approx.

The physico-chemical properties of N,N'-bis(2-hydroxyethyl)-dodecenediamide disuccinate acid were as follows:

| | |
|---|---|
| physical state | white amorphous powder |
| molecular formula | $C_{24}H_{38}N_2O_{10}$ |
| molecular weight | 514.58 |
| elemental analysis | C = 56.02%; H = 7.44%; N = 5.44%; O = 31.09% |
| solubility in organic solvents | >10 mg/ml in DMSO |
| solubility in water | poorly soluble (>1 mg/ml in 50 mM phosphate buffer, pH 7.4, NaCl 0.9%) |
| TLC | eluent: chloroform-methanol-water-$NH_3$ (30%), 50/40/7/3 Rf = 0.56 |

EXAMPLE 9

Preparation of N,N'-Bis-(2-Hydroxyethyl)-Nonandiamide

A mixture of acrylic acid (1.88 g; 10 mmol) and ethanolamine (1.84 g; 30 mmol) was fed to a flask provided with reflux condenser and heated to 160° C., for 6 hrs, on an oil bath.

The reaction mixture was crystallized from isopropanol (50 ml). The crystalline fraction was separated by filtration, washed three times with cold isopropanol and finally dried in high vacuo.

The reaction yield was 78% approx.

The physico-chemical properties of N,N'-bis(2-hydroxyethyl)-nonandiamide were as follows:

| | |
|---|---|
| physical state | white crystalline powder |
| molecular formula | $C_{13}H_{26}N_2O_4$ |
| molecular weight | 274.37 |
| elemental analysis | C = 56.91%; H = 9.55%; N = 9.55%; O = 23.3% |
| solubility in organic solvents | >10 mg/ml in DMSO |
| melting point | 132–134° C. |
| TLC | eluent: chloroform-methanol-water-$NH_3$ (28%), 80/25/2/1 Rf = 0.48 |

EXAMPLE 10

Preparation of N-(2-Hydroxyethyl)-Arachidonamide

A mixture of arachidonic acid (3.04 g; 10 mmol) and triethanolamine (10.6 g; 10.5 mmol) in anhydrous THF (100 ml) was stirred under nitrogen atmosphere, added dropwise over a period of 30 minutes to a solution of isobutylchloroformate (1.44 g; 10.5 mmol) in THF (50 ml). The resulting mixture was stirred at −10° C. for 2 hrs and then at 0° C. for 5 hrs, and added dropwise with ethanolamine (0.9 g; 14.7 mmol). The resulting mixture was stirred at 0° C. for over 2 hrs and finally evaporated to dryness. The crude residue was purified by chromatography eluting with a 98:2 v/v chloroform-methanol mixture. The eluate fractions were combined and evaporated to dryness; the residue was dried in vacuo.

The physico-chemical properties of N(2-hydroxyethyl)-arachidonamide were as follows:

| | |
|---|---|
| physical state | colourless oil |
| molecular formula | $C_{22}H_{37}NO_2$ |
| molecular weight | 347.54 |
| elemental analysis | C = 76.03%; H = 10.73%; N = 4.03%; O = 9.21% |
| solubility in organic solvents | >10 mg/ml in DMSO; >10 mg/ml in ethanol |
| solubility in water | poorly soluble |
| TLC | eluent: chloroform-methanol-water-$NH_3$ (28%), 80/25/2/1<br>Rf = 0.66 |

BIOLOGICAL ACTIVITY

In vitro evaluation of the neuroprotective effect against excitotoxicity of Excitatory Amino Acids in primary neuronal cultures of the following compounds was carried out:

Compound a: N-(2-hydroxyethyl)-palmitoylamide (Example 1)

Compound b: N-palmitoylethanolamide phosphate (Example 5)

Compound c: N-(2-hydroxyethyl)-arachidonamide (Example 10)

Compound d: N,N'-bis-(2-hydroxyethyl)-nonanediamide (Example 9)

Materials and Methods

Compounds Solubilization

The compounds under evaluation, referred to as a, b, c, and d, were solubilized in DMSO and culture medium to obtain concentrations of 100 $\mu$M (4% DMSO) and 60 $\mu$M (3% DMSO) and added to the culture mediums according to different treatment schedules in order to determine the time-effect relationship vs. the incubation time and the exposure to the neurotoxic stimulus.

Cultures Preparation

Granular cell cultures were obtained from postnatal day 8–9 mouse Balb-6 cerebellum. The cells were suspended in EBM+2 mM L-glutamine, 100 U/ml penicillin, 50 $\mu$g/l gentamicin, 25 mM KCl and 10% fetal calf serum, plated on polylysine substrate, cultured for 8–10 days and then exposed to Glu 500 $\mu$M at room temperature for 5 min. The compounds being evaluated were added to the cultures at the same time of exposure, soon after exposure or 15 min after exposure to Glu, and cultured for 60 minutes; cultures were then washed and brought back to the original medium. The number of survived cells was evaluated by calorimetric method (MTT) 24 hours after excitotoxic stimulation.

Results

The tested compounds exert a protective action against the excitotoxic stimulus at the two concentrations tested (100 and 60 $\mu$M), independently of the treatment scheme adopted, that is when incubated at the same time of exposure, soon after exposure or 15 min after exposure to Glu, as shown in Table 1. Furthermore, they do not show any significant intrinsic cytotoxicity.

Said experimental evidences suggest that the aforesaid molecules exert a protective action within very short times and affect not only the cytotoxic events mediated by an overstimulation of NMDA receptor, but above all, being active during post-treatment, the cytotoxic mechanisms following receptor activation, thus concurring for example to limit calcium ions influx into the cell and the consequent processes leading to cellular death.

TABLE 1

Protective effect against cellular death induced by Glu (500 $\mu$M for 5 min) of compound a, b, c and d, incubated at the concentrations of 60 and/or 100 $\mu$M and added to the cells:
A: at the same time of exposute to Glu;
B: soon after exposure to Glu;
C: 15 min after exposure to Glu.
Cell survival is expressed as a percentage of control values. Each value is the average of three tests. Incubation with 4% DMSO does not affect cell survival.

| | survived cells (%) | |
|---|---|---|
| Treatment | 100 $\mu$M | 60 $\mu$M |
| Control values | 100 | 100 |
| Glu | 40 | 44 |
| A: | | |
| + Compound a | 67 | 86 |
| + Compound b | n.d. | 68 |
| + Compound c | n.d. | 95 |
| + Compound d | 68 | n.d. |
| B: | | |
| + Compound a | 84 | n.d. |
| + Compound b | n.d. | 99 |
| + Compound d | 92 | n.d. |
| C: | | |
| + Compound a | 76 | 101 |
| + Compound b | n.d. | 90 |
| + Compound d | 87 | n.d. |

Conclusions

As a whole, the above experimental evidences show that N-acyl derivatives of mono and dicarboxylic acids with amino alcohols according to the present invention are able, even at low concentrations, to exert a specific protective action against the neurotoxicity of Excitatory Amino Acids on neuronal cells. Particular notice has to be given to the outstanding therapeutic significance of said molecules, in that i) they are characterized by an extremely prompt effect and ii) they are active when administered at the same time or more importantly after exposure to excitatory amino acids, thus affecting not only the short-term neurotoxic mechanisms mediated by the activation of glutamic or kainic acid receptors, but also one or more events downstream of receptor overstimulation. Furthermore, the compounds do not show any significant intrinsic cytotoxicity.

Therefore, the derivatives described herein can be advantageously used in the treatment of CNS disorders of humans and animals, whose etiology/evolution is associated with the hyper stimulation of excitatory amino acid receptors, in particular the NMDA receptor.

In fact, under physiological conditions, Excitatory Amino Acids (EAA) mediate synaptic transmission, involved in the phenomena of neuronal plasticity underlying behavioural and cognitive processes, and in motor functions. Under particular conditions of hyper stimulation, they are responsible for a neuronal damage that may ultimately result in neuronal death. There is evidence for a correlation between overstimulation of NMDA receptors and CNS damage associated with acute events, such as hypoxia-ischemia, stroke, hypoglycemia, perinatal anoxia, epilepsy, brain and spinal cord injuries, neurolathyrism, or in chronic neurodegenerative disorders, such as Hungtington's Chorea, Alzheimer's and Parkinson's diseases, amyotrophic lateral sclerosis, and pontocerebellar degeneration (J. W. Olney, "Excitotoxic Amino Acids and Neuropsychiatric Disorders", Ann.Rev.Pharmacol.Toxicol., 30: 47–71, 1990) or neurological complications associated with viral diseases, such as HIV-1 infection (AIDS dementia complex) (M. P. Heyes et al., "Quinolinic Acid in Cerebrospinal fluid and serum in HIV-1 Infection: Relationship to Clinical and Neurological Status", Ann.Neurol., 29: 202–209, 1991).

Further disturbances of the glutamatergic system are known to have a remarkable consequence for hypothalamic homeostasis and on processes derived therefrom (A. N. Van den Pol and P. Q. Trombley, "Glutamate Neurons in Hypothalamus regulate Excitatory Transmission", The J. of Neuroscience, 13(7): 2829–2836, 1993).

It should be emphasized that currently available therapies are of limited value in the acute phase of diseases such as cerebral ictus, which have an extremely narrow "therapeutic window" in terms of the time frame during which neuronal cell death can be limited by pharmacological intervention. In this context, it is of great significance that the molecules of the present invention are capable of acting not only within this very short time of damage induction, but also later on when the damage has been already established. Further, since said new derivatives do not act like NMDA-receptor competitive or non-competitive inhibitors, they may effectively be used also to treat chronic diseases such as Hungtington's Chorea, Parkinson's disease and conditions involving dementia without affecting plastic phenomena and thus, unlike NMDA receptor inhibitors, would not be expected to worsen the clinical outcome.

It needs to be remembered that dosages, times and routes of administration will vary depending on the disease type, stage and severity. A distinction is to be made between treatment of:
 i) acute conditions (hypoxia-ischemia, stroke, brain and spinal cord injury, hypoglycemia, cerebral hypoxic states associated with cardiovascular surgery) or diseases inducing a prompt and massive Glu release, such as epilepsy, transient ischemic attacks (TIA), neurolathyrism;
 ii) chronic degenerative diseases such as Hungtington's Chorea, Alzheimer's and Parkinson's diseases, amyotrophic lateral sclerosis and dementia, either primary or associated with other pathologies even of viral origin, such as acquired immunodeficiency syndrome (AIDS dementia complex).

Further, primary retinic diseases even of anoxic nature or associated with eye hypertension, e.g. glaucoma, are to be taken into consideration. For all aforesaid diseases, the compounds according to the present invention can be administered by systemic oral or parenteral routes, or by topical or transdermic routes.

The therapeutic dose varies, depending on the patient's age and weight as well as on the type of disease, from 0.1 to 100 mg/kg/day, preferably from 1 to 30 mg/kg/day, over variable periods depending on the disease, in any case for at least 30 days.

The pharmaceutical compositions are inclusive of all formulations containing pharmaceutically acceptable excipients, that are suitable for the administration of the claimed active ingredients in the forms best suited to the disease to be treated and, in any case, rendering the active ingredients as bioavailable as possible. In particular, injectable solutions for general intravenous, subcutaneous and intramuscular administration and solutions for ophthalmic treatment are to be envisaged. As concerns the formulations per os granular powders, tablets, pills and capsules are the preferred ones.

EXAMPLE 1

Tablets

Every tablet contains:

| | |
|---|---|
| N-palmitoylethanolamide | 300 mg |
| cellulose | 40 mg |
| lactose | 120 mg |
| sodium carboxymethylamide | 25 mg |
| precipitated silica | 20 mg |
| polyvinylpyrrolidone | 16.66 mg |
| maize starch | 13.00 mg |
| Tween 20 | 7.14 mg |
| magnesium stearate | 6.20 mg |

EXAMPLE 2

Vials for Injection

Every vial contains:

| | |
|---|---|
| lyophilized N,N'-bis--(2-hydroxyethyl)-nonandiamide to be taken up in buffer solution: | 10 mg |
| dibasic sodium phosphate 12 $H_2O$ | 6 mg |
| monobasic sodium phosphate 2 $H_2O$ | 6 mg |
| sodium chloride | 16 mg |
| Water for injectable formulations | q.s. to 2 ml |

EXAMPLE 3

Gelatin Capsules

Every capsule contains:

| | |
|---|---|
| N-arachidonylethanolamide | 50 mg |
| O.P. peanut oil | 100 mg |
| O.P. gelatin | 52 mg |
| O.P. glycerin | 16 mg |
| erythrosine (E127) | 0.1 mg |

EXAMPLE 4

Gel for Ophtalmic Use

Every tube contains 5 g of product having the following composition:

| | |
|---|---|
| w/w N,N'-bis-(2-hydroxyethyl)-nonandiamide (as per Example 9) | 4 g |

| | |
|---|---|
| benzalconium chloride | 0.008 g |
| carbopol 940 | 3.5 g |
| disodium edetate | 0.01 g |
| hydrochloric acid/sodium hydroxyde | q.s. to pH 5 |
| purified water | q.s. to 100 g |

In conclusion, the compounds of the present invention, when adequately formulated, may be conveniently used in human and animal therapy for the treatment of diseases in which acute or chronic neurological damage is directly or indirectly due to excitotoxic phenomena, such as caused by Glu or related toxins. Said diseases are e.g.: hypoxic and/or ischemic cerebral insults, hypoxic and/or ischemic acute or recurrent and transient attacks, such as TIA; brain or spinal cord injuries; neurodegenerative disorders of unknown etiology (Alzheimer's and Parkinson's diseases, Huntington's Chorea, amyotrophic lateral sclerosis), or derived from neuronal disturbances following epilepsy and severe hypoglycemic states; neurological complications whose primary cause is an infection (e.g. HIV); neurological complications following hypoxic states caused by cardiovascular surgery or heart failure; diseases pertaining to the retina and in general to the visual system, as well as pertaining to other cranial nerves, e.g. nerves afferent to the auditory system, and neurological diseases following excitotoxic damage due to toxic agents e.g. neurolathyrism.

We claim:

1. A method for treating or preventing neurotoxicity induced by excitatory amino acids in a subject, comprising administering to the subject an effective amount of the compound N,N'-bis-(2-hydroxyethyl)-nonandiamide.

2. The method according to claim 1, wherein said neurotoxicity is associated with a disease selected from the group consisting of hypoxia-ischemia, stroke, brain and spinal cord injuries, epilepsy, transient ischemic attacks, neurolathyrism, amyotrophic lateral sclerosis, Huntington's Chorea, Alzheimer's disease, primary dementia, dementia associated with viral infections, and anoxia-ischemic diseases of the retina.

3. The method according to claim 1, wherein said compound is orally administered in the form of a granular powder, tablet, pill or capsule.

4. The method according to claim 1, wherein said compound is administered intravenously, subcutaneously or intramuscularly.

5. The method according to claim 1, wherein said compound is administered for ophthalmic use in the form of drops or ointments.

6. The method according to claim 1, wherein said compound is administered topically or transdermally.

7. The method according to claim 1, wherein said compound is administered at a dosage in the range of 0.1 to 100 mg/kg/day for at least 30 days.

8. The method according to claim 7, wherein said dosage ranges from 1 to 30 mg/kg/day.

* * * * *